United States Patent
Fantuzzi

(10) Patent No.: US 8,147,826 B2
(45) Date of Patent: Apr. 3, 2012

(54) METHOD OF MAKING A SOFT GEL CAPSULE COMPRISING COQ-10 SOLUBILIZED IN A MONOTERPENE

(75) Inventor: Michael Fantuzzi, Glendale, CA (US)

(73) Assignee: Soft Gel Technologies, Inc., Los Angeles, CA (US)

( * ) Notice: Subject to any disclaimer, the term of this patent is extended or adjusted under 35 U.S.C. 154(b) by 0 days.

(21) Appl. No.: 11/223,718

(22) Filed: Sep. 9, 2005

(65) Prior Publication Data

US 2006/0013888 A1    Jan. 19, 2006

Related U.S. Application Data

(63) Continuation of application No. 10/674,268, filed on Sep. 29, 2003.

(51) Int. Cl.
*A61K 38/43* (2006.01)
*A61K 31/122* (2006.01)
*A61K 31/05* (2006.01)
*A61K 9/66* (2006.01)

(52) U.S. Cl. ....... 424/94.1; 514/688; 514/731; 424/455; 424/452

(58) Field of Classification Search ............... 424/94.1, 424/455, 452; 514/688, 731
See application file for complete search history.

(56) References Cited

U.S. PATENT DOCUMENTS

| | | | |
|---|---|---|---|
| 4,029,760 A | 6/1977 | De Roeck born Holtzhauer | |
| 4,343,816 A | 8/1982 | Cavazza | |
| 4,559,222 A | 12/1985 | Enscore et al. | |
| 4,565,700 A * | 1/1986 | Suzuki ........................ | 424/757 |
| 4,599,232 A | 7/1986 | Bertelli | |
| 4,687,782 A | 8/1987 | Brantman | |
| 4,824,669 A * | 4/1989 | Folkers et al. ............... | 424/94.1 |
| 5,030,458 A | 7/1991 | Shug et al. | |
| 5,240,961 A | 8/1993 | Shug | |
| 5,290,605 A | 3/1994 | Shapira | |
| 5,298,246 A | 3/1994 | Yano et al. | |
| 5,310,578 A * | 5/1994 | Thurn-Muller et al. ...... | 427/220 |
| 5,362,753 A | 11/1994 | Blum et al. | |
| 5,378,461 A | 1/1995 | Neigut | |
| 5,391,550 A | 2/1995 | Carniglia et al. | |
| 5,431,916 A | 7/1995 | White | |
| 5,500,416 A | 3/1996 | Miyazawa et al. | |
| 5,504,072 A | 4/1996 | Schmidl et al. | |
| 5,512,691 A | 4/1996 | Barnicki et al. | |
| 5,532,002 A | 7/1996 | Story | |
| 5,552,167 A | 9/1996 | Taylor et al. | |
| 5,560,928 A | 10/1996 | Defelice | |
| 5,591,772 A | 1/1997 | Lane et al. | |
| 5,626,849 A | 5/1997 | Hastings et al. | |
| 5,637,316 A | 6/1997 | Ribier et al. | |
| 5,645,856 A | 7/1997 | Lacey et al. | |
| 5,670,320 A | 9/1997 | Wallace et al. | |
| 5,686,491 A | 11/1997 | Sherwood | |
| 5,716,928 A | 2/1998 | Benet et al. | |
| 5,756,291 A | 5/1998 | Griffin | |
| 5,843,476 A | 12/1998 | Ribier et al. | |
| 5,858,401 A | 1/1999 | Bhalani et al. | |
| 5,889,062 A | 3/1999 | Hoppe et al. | |
| 5,891,469 A | 4/1999 | Amselem | |
| 5,912,272 A | 6/1999 | Hoppe et al. | |
| 5,916,591 A | 6/1999 | Bierdel-Willkommen | |
| 5,948,443 A | 9/1999 | Riley et al. | |
| 5,968,987 A | 10/1999 | Charman et al. | |
| 5,976,568 A | 11/1999 | Riley | |
| 5,977,162 A | 11/1999 | Seidman | |
| 5,980,939 A | 11/1999 | Kim et al. | |
| 5,985,344 A | 11/1999 | Cherukuri et al. | |
| 6,008,192 A | 12/1999 | Al-Razzak et al. | |
| 6,020,383 A | 2/2000 | Stone et al. | |
| 6,033,678 A | 3/2000 | Lorenzen | |
| 6,048,846 A | 4/2000 | Cochran | |
| 6,048,886 A | 4/2000 | Neigut | |
| 6,054,136 A | 4/2000 | Farah et al. | |
| 6,056,971 A | 5/2000 | Goldman | |
| 6,063,432 A | 5/2000 | Maxwell et al. | |
| 6,069,167 A | 5/2000 | Sokol | |
| 6,080,788 A | 6/2000 | Sole et al. | |
| 6,096,338 A | 8/2000 | Lacy et al. | |
| 6,121,234 A | 9/2000 | Benet et al. | |
| 6,174,547 B1 | 1/2001 | Dong et al. | |
| 6,184,255 B1 | 2/2001 | Mae et al. | |
| 6,197,349 B1 | 3/2001 | Westesen et al. | |
| 6,200,550 B1 | 3/2001 | Masterson et al. | |
| 6,203,818 B1 | 3/2001 | Vester | |
| 6,207,137 B1 | 3/2001 | Shuch et al. | |

(Continued)

FOREIGN PATENT DOCUMENTS

DE        3512054        10/1986

(Continued)

OTHER PUBLICATIONS

Oilseeds International Ltd., Rice bran oil—a health benefit, http://www. oilseedssf.com/products/prod_rice.html, 2002, printed on Mar. 6, 2006.* Merriam-Webster Dictionary OnLine, definition of "elixir," http://www.merriam-webster.com/dictionary/elixir, printed from the Jun. 3, 2009, 2 pages.
Amendment and Response to Office Action dated Oct. 19, 2009, U.S. Appl. No. 10/674,268, 11 pages.
Amendment and Response to Office Action dated Sep. 22, 2009, U.S. Appl. No. 10/963,328 11 pages.
Notice of Allowance and Fee(s) Due dated Aug. 7, 2009, U.S. Appl. No. 11/860,232, 17 pages.
Examiner's Interview Summary dated Feb. 23, 2010, U.S. Appl. No. 10/674,268, 4 pages.
Notice of Appeal and Interview Summary dated May 18, 2010, U.S. Appl. No. 10/674,268, 2 page.
Examiner's Interview Summary dated May 20, 2010, U.S. Appl. No. 10/674,268, 4 pages.
Request for Continued Examination, Amendment and Response to Final Office Action, dated Dec. 17, 2010, U.S. Appl. No. 10/674,268,12 pages.
Notice of Appeal dated Feb. 23, 2010, U.S. Appl. No. 10/953,328, 1 page.

(Continued)

*Primary Examiner* — Rosanne Kosson
(74) *Attorney, Agent, or Firm* — Dorsey & Whitney LLP

(57) ABSTRACT

The present invention is directed to compositions and methods of delivery of CoQ-10 solubilized in monoterpenes. Use of monoterpenes as dissolving agents, greatly effects the ability to incorporate greater amounts of bioactive CoQ-10 in formulations, such as soft gel capsules.

15 Claims, No Drawings

U.S. PATENT DOCUMENTS

| | | |
|---|---|---|
| 6,232,346 B1 | 5/2001 | Sole et al. |
| 6,261,575 B1 | 7/2001 | Hoppe et al. |
| 6,267,985 B1 | 7/2001 | Chen et al. |
| 6,277,431 B1 | 8/2001 | Berry et al. |
| 6,284,268 B1 | 9/2001 | Mishra et al. |
| 6,300,361 B1 | 10/2001 | Vivilecchia et al. |
| 6,300,377 B1 | 10/2001 | Chopra |
| 6,335,361 B1 | 1/2002 | Hamilton |
| 6,342,526 B1 | 1/2002 | Vervuert et al. |
| 6,365,181 B1 | 4/2002 | Matthews |
| 6,368,618 B1 | 4/2002 | Jun et al. |
| 6,426,362 B1 | 7/2002 | Miller et al. |
| 6,428,779 B1 | 8/2002 | Sauermann et al. |
| 6,436,431 B1 | 8/2002 | Hoffpauer et al. |
| 6,441,050 B1 | 8/2002 | Chopra |
| 6,455,589 B1 | 9/2002 | Ames et al. |
| 6,469,024 B2 | 10/2002 | Tino et al. |
| 6,472,378 B2 | 10/2002 | von Borstel |
| 6,479,069 B1 | 11/2002 | Hamilton |
| 6,503,483 B2 | 1/2003 | Shuch et al. |
| 6,503,506 B1 | 1/2003 | Germano |
| 6,503,523 B2 | 1/2003 | Hoppe et al. |
| 6,506,915 B1 * | 1/2003 | West ............... 552/293 |
| 6,528,042 B1 | 3/2003 | Brown et al. |
| 6,545,184 B1 | 4/2003 | Lipshutz |
| 6,552,004 B1 | 4/2003 | Elazhary et al. |
| 6,562,869 B1 | 5/2003 | Hamilton et al. |
| 6,569,463 B2 | 5/2003 | Patel et al. |
| 6,579,854 B1 | 6/2003 | Mitchell et al. |
| 6,616,942 B1 | 9/2003 | Udell |
| 6,623,734 B2 | 9/2003 | Udell et al. |
| 6,630,170 B2 | 10/2003 | Balkus et al. |
| 6,664,287 B2 | 12/2003 | Avery et al. |
| 6,730,319 B2 | 5/2004 | Maeder et al. |
| 6,740,338 B1 | 5/2004 | Chopra |
| 6,782,307 B2 | 8/2004 | Wilmott et al. |
| 6,790,465 B2 | 9/2004 | Weissman |
| 6,855,733 B2 | 2/2005 | Udell et al. |
| 6,955,820 B1 | 10/2005 | Udell |
| 7,015,245 B2 | 3/2006 | Rich et al. |
| 7,026,361 B2 | 4/2006 | Minemura et al. |
| 7,060,263 B2 | 6/2006 | Udell et al. |
| 7,169,385 B2 | 1/2007 | Fantuzzi et al. |
| 7,182,950 B2 | 2/2007 | Garti et al. |
| 7,220,429 B2 | 5/2007 | Udell |
| 7,273,606 B2 | 9/2007 | Fantuzzi et al. |
| 7,273,622 B2 | 9/2007 | Udell et al. |
| 7,588,786 B2 | 9/2009 | Khan et al. |
| 7,713,523 B2 | 5/2010 | Fantuzzi et al. |
| 2002/0048798 A1 | 4/2002 | Avery et al. |
| 2002/0098172 A1 | 7/2002 | Udell et al. |
| 2003/0082168 A1 | 5/2003 | Yegorova |
| 2003/0108600 A1 | 6/2003 | Okibayashi et al. |
| 2003/0119781 A1 | 6/2003 | Udell et al. |
| 2003/0147927 A1 | 8/2003 | Khan et al. |
| 2003/0176500 A1 | 9/2003 | Molly et al. |
| 2003/0232076 A1 | 12/2003 | Makino et al. |
| 2003/0232095 A1 * | 12/2003 | Garti et al. ............... 424/725 |
| 2004/0001874 A1 * | 1/2004 | Davidson et al. ............ 424/439 |
| 2004/0047922 A1 * | 3/2004 | Elstner .............. 424/736 |
| 2004/0126432 A1 | 7/2004 | Hennen |
| 2004/0166157 A1 | 8/2004 | Thombre |
| 2005/0025756 A1 * | 2/2005 | Erwin ............... 424/94.1 |
| 2005/0031681 A1 | 2/2005 | Udell et al. |
| 2005/0036998 A1 | 2/2005 | Udell |
| 2005/0037066 A1 | 2/2005 | Udell et al. |
| 2005/0069582 A1 | 3/2005 | Fantuzzi |
| 2005/0070611 A1 | 3/2005 | Fantuzzi |
| 2005/0169983 A1 | 8/2005 | Hassan et al. |
| 2007/0269508 A1 | 11/2007 | Udel |
| 2008/0003279 A1 | 1/2008 | Udell |
| 2008/0020022 A1 | 1/2008 | Udell |
| 2008/0089877 A1 | 4/2008 | Udell et al. |
| 2008/0152707 A1 | 6/2008 | Fantuzzi et al. |
| 2008/0226710 A1 | 9/2008 | Fantuzzi |

FOREIGN PATENT DOCUMENTS

| | | |
|---|---|---|
| EP | 0 882 450 | 1/1998 |
| EP | 888774 A2 * | 1/1999 |
| EP | 1 728 506 | 3/2006 |
| JP | 55081813 | 6/1980 |
| JP | 57042616 | 3/1982 |
| JP | S57042616 | 3/1982 |
| JP | 5770815 | 5/1982 |
| JP | S57142911 | 9/1982 |
| JP | 59172417 | 9/1984 |
| WO | WO 88/03015 | 5/1988 |
| WO | WO 98/40086 | 9/1998 |
| WO | WO 98/56368 | 12/1998 |
| WO | WO 00/51574 | 9/2000 |
| WO | WO 02/09685 | 2/2002 |
| WO | WO 03/105607 | 12/2003 |
| WO | WO 2004/066925 | 8/2004 |
| WO | WO 2005/032278 | 4/2005 |
| WO | WO 2005/092123 | 10/2005 |

OTHER PUBLICATIONS

Appeal Brief dated Apr. 23, 2010, U.S. Appl. No. 10/953,328, 49 pages.

Examiner's Answer dated May 24, 2010, U.S. Appl. No. 10/953,328, 8 pages.

Final Office Action dated Nov. 18, 2009, U.S. Appl. No. 10/674,268, 11 pages.

Final Office Action dated Oct. 23, 2009, U.S. Appl. No. 10/963,328, 9 pages.

Anderson U.S. Appl. No. 60/253,874, David M. Anderson, Applicant, filed Nov. 29, 2000, 21 pages.

Al-Hasso, Shahla, "Coenzyme Q10: A Review," *Hospital Pharmacy*, vol. 36, No. 1, pp. 51-55, 2000 Facts and Comparisons.

COMAX Q10 Trademark Registration Abstract and Specimen, Registration No. 1764014, registered Apr. 13, 1993, 26 pages.

Constantinescu, et al., "A Randomized Study of the Bioavailability of Different Formulations of Coenzyme Q10 (Ubiquinon)," The Journal of Clinical Pharmacology, 2007; 47: 1580-1586.

Kang et al., "Physicochemical studies of lidocaine-menthol binary systems for enhanced membrane transport," *International Journal of Pharmaceutics*, 206 (2000) 35-42.

Kommuru, et al., "A simplified chromatographic method for quantitative determination of coenzyme Q10 in dog plasma," *Journal of Pharmaceutical and Biomedical Analysis*, 16 (1998) 1037-1040.

Nazzal et al., "Preparation and in vitro characterization of a eutectic based semisolid self-nanoemulsified drug delivery system (SNEDDS) of ubiquinone: mechanism and progress of emulsion formation," *International Journal of Pharmaceutics*, 235 (2002) 247-265.

Nazzal et al., "Response Surface Methodology for the Optimization of Ubiquinone Self-Nonoemulsified Drug Delivery System," *AAPSPharmSciTech 2002*; 3 (1) *article 3*, pp. 1-9, Published: Feb. 8, 2002, found at URL: http://www.aapspharmscitech.org.

Pouton, Colin W., "Lipid formulations for oral administration of drugs: non-emulsifying, self-emulsifying and 'self-microemulsifying' drug delivery systems," *European Journal of Pharmaceutical Sciences* 11 Suppl. 2 (2000) S93-S98.

Shojaei et al., "Transbuccal permeation of a nucleoside analog, dideoxycytidine: effects of menthol as a permeation enhancer," *International Journal of Pharmaceutics* 192 (1999) 139-146.

Shrestha et al., "Aqueous Phase Behavior of Diglycerol Fatty Acid Esters," *Journal of Dispersion Science and Technology*, 28: pp. 883-891, 2007.

Siekmann et al., "Preparation and Physicochemical Characterization of Aqueous Dispersions of Coenzyme Q10 Nanoparticles," *Pharmaceutical Research*, vol. 12, No. 2, 1995.

Weber, et al., "Intestinal Absorption of Coenzyme Q10 Administered in a Meal or as Capsules to Healthy Subjects," *Nutrition Research*, vol. 17, No. 6, pp. 941-945, 1997.

Office Action dated Jan. 12, 2011, U.S. Appl. No. 10/674,268, 14 pages.

Amendment and Response to Office Action dated Jun. 13, 2011, U.S. Appl. No. 10/674,268, 13 pages.

Decision on Appeal dated May 11, 2011, U.S. Appl. No. 10/953,328, 9 pages.
Office Action dated May 18, 2011, U.S. Appl. No. 10/953,328, 9 pages.
Author Unknown, "pformulate: A Soft Gell!!" 2000, pp. 1-6, found at URL: http://www.pformulate.com/pformsoftgel.htm.
Author Unknown, Paul Karrer Biography, Nobel Prizes, Nobel Prize in Chemistry, nobelprize.org, printed on Jan. 5, 2007, 2 pages.
Kaplun-Frischoff, et al., "Testosterone Skin Permeation Enhancement by Menthol through Formation of Eutectic with Drug and Interaction with Skin Lipids," Journal of Pharmaceutical Sciences, vol. 86, No. 12, Dec. 1997, pp. 1394-1399.
Kommuru, et al., "Racemate and Enantiomers of Ketoprofen: Phase Diagram, Thermodynamic Studies, Skin Permeability, and Use of Chiral Permeation Enhancers," *Journal of Pharmaceutical Sciences* vol. 87, No. 7, Jul. 1998, pp. 833-840.
Office Action dated Jul. 6, 2011, U.S. Appl. No. 10/674,268, 12 pages.
Amendment and Responses to Office Action and Terminal Disclaimer dated Aug. 18, 2011, U.S. Appl. No. 10/953,328, 9 pages.
Terminal Disclaimer dated Sep. 2, 2011, U.S. Appl. No. 10/953,328, 2 pages.
Notice of Allowance and Fee(s) Due dated Sep. 21, 2011, U.S. Appl. No. 10/953,328, 11 pages.
International Search Report dated Feb. 2, 2005, PCT/US2004/031775 [WO 05/032278], 3 pages.
International Search Report dated May 3, 2005, PCT/US2005/004781 [WO 05/092123], 3 pages.
Author Unknown, Paul Karrer Biography, Nobel Prizes, Nobel Prize in Chemistry, nobelprize.org, printed on Jan. 5, 2007, 1 page.
Bhandari, et al., "Preparation, Characterization and Evaluation of Coenzyme Q10 Binary Solid Dispersions for Enhanced Solubility and Dissolution," *Biol Pharm. Bull.*, 2007, vol. 30, No. 6, pp. 1171-1176.
Bliznakov, et al., "Biochemical and Clinical Consequencs of Inhibiting Coenzyme Q10 Biosynthesis by Lipid-Lowering HMG-CoA Reductase Inhibitors (Statins): A Critical Overview," *Advances in Therapy*, Jul./Aug. 1998, vol. 15, No. 4, pp. 218-228.
Chopra, et al., "Relative Bioavailability of Coenzyme Q10 Formulations in Human Subjects," *Internat. J. Vit. Nutr. Res.*, 1998, vol. 68, pp. 109-113.
Chopra, et al., "A New Coenzyme Q10 Preparation with Enhanced Bioavailability," *FASEB Journal*, 1997, vol. 11, No. 3, pp. A586 (Abstract).
CRC Handbook of Chemistry and Physics, 51st Edition, R.C. Weast (Editor), The Chemical Rubber Co., Cleveland, Ohio, 1970, pp. C-309, 356, 364, 392, 434 and 488.
Density of Cooking Oil, *The Physics Factbook*, edited by Glenn Elert, dated unknown, 3 pages.
Dictionary.com accessed on Jan. 17, 2007, "thixotropic" 1 page.
Grant & Hackh's Chemical Dictionary, Definition of Gelatin, Fifth Edition, McGraw-Hill Book Company, 1987, p. 258.
Greenberg, et al., "Co-enzyme Q10: a new drug for cardiovascular disease," *The Journal of Clinical Pharmacology*, 1990, vol. 30, pp. 596-608.
Kommuru, et al., "Self-emulsifying drug delivery systems (SEDDS) of coenzyme Q10: formulation development and bioavailabiilty assessment," *International Journal of Pharmaceutics*, 2001, vol. 212, pp. 233-246.
Padilla-Zakour, "Chemical Food Preservatives: Bonzoate and sorbate," *Venture*, New York State Agriculture Experimental Station, 1998, vol. 1, No. 2, 3 pages, found at URL: http://www.nysaes.cornell.edu/necfe/pubs/pdf/Venture/venture2_chemical.html.
RITO Partnership, Rice Bran Oil Info, http://web.archive.org/web/20020809203831/http://www.ricebranoil.info/why/index.html, web page of Aug. 9, 2002, printed from the Internet on Apr. 29, 2009.
Walker, "Mass, Weight, Density or Specific Gravity of Liquids, Specific Gravity of Liquids," 2007, Slmetric.co.uk [http://www.simetric.co.uk/si_liquids.htm], 5 pages.
Weis, et al., "Bioavailability of Four Oral Coenzyme Q10 Formulations in Health Volunteers," *Molec. Aspects. Med.*, 1994, vol. 15, Supplement, pp. s273-s280.

Office Action (Restriction Requirement) dated Jan. 7, 2005, U.S. Appl. No. 10/674,268, 9 pages.
Response to Restriction Requirement dated Feb. 7, 2005, U.S. Appl. No. 10/674,268, 2 pages.
Office Action dated Mar. 11, 2005, U.S. Appl. No. 10/674,268, 8 pages.
Amendment and Response under 37 C.F.R. 1.111 dated Jun. 7, 2005, U.S. Appl. No. 10/674,268, 10 pages.
Office Action (Restriction Requirement) dated Jun. 28, 2005, U.S. Appl. No. 10/674,268, 7 pages.
Response to Restriction Requirement dated Jul. 27, 2005, U.S. Appl. No. 10/674,268, 10 pages.
Notice of Allowance and Fee(s) Due dated Aug. 26, 2005, U.S. Appl. No. 10/674,268, 11 pages.
Request for Continued Examination dated Sep. 15, 2005, U.S. Appl. No. 10/674,268, 1 page.
Declaration Under 37 C.F.R. 1.131 Antedating a Reference, dated Sep. 15, 2005, U.S. Appl. No. 10/674,268, 2 pages.
Office Action dated Sep. 30, 2005, U.S. Appl. No. 10/674,268, 8 pages.
Amendment and Response dated Dec. 20, 2005, U.S. Appl. No. 10/674,268, 13 pages.
Final Office Action dated Jan. 31, 2006, U.S. Appl. No. 10/674,268, 7 pages.
Response to Office Action Made Final, dated Apr. 28, 2006, U.S. Appl. No. 10/674.268, 14 pages.
Advisory Action dated May 22, 2006, U.S. Appl. No. 10/674,268, 4 pages.
Notice of Appeal dated May 31, 2006, U.S. Appl. No. 10/674,268, 2 pages.
Request for Continued Examination and Response to Office Action Made Final and Advisory Action dated Aug. 31, 2006, U.S. Appl. No. 10/674,268, 14 pages.
Final Office Action dated Sep. 15, 2006, U.S. Appl. No. 10/674,268, 8 pages.
Notice of Appeal dated Mar. 15, 2007, U.S. Appl. No. 10/674,268, 2 pages.
Request for Continued Examination and Response to Office Action Made Final dated Jul. 12, 2007, 16 pages.
Final Office Action dated Aug. 2, 2007, U.S. Appl. No. 10/674,268, 9 pages.
Response to Office Action Made Final, dated Oct. 8, 2007, U.S. Appl. No. 10/674,268, 11 pages.
Declaration Under Rule 1.131, dated Oct. 8, 2007, U.S. Appl. No. 10/674,268, 30 pages.
Advisory Action dated Oct. 25, 2007, U.S. Appl. No. 10/674,268, 14 pages.
Request for Continued Examination dated Oct. 30, 2007, U.S. Appl. No. 10/674,268, 2 pages.
Declaration Under Rule 1.131 dated Feb. 12, 2008, U.S. Appl. No. 10/674,268, 2 pages.
Interview Summary dated Mar. 3, 2008, U.S. Appl. No. 10/674,268, 3 pages.
Final Office Action dated Apr. 10, 2008, U.S. Appl. No. 10/674,268 6 pages.
Amendment and Response to Final Office Action dated Sep. 22, 2008, 17 pages.
Advisory Action dated Sep. 30, 2008, U.S. Appl. No. 10/674,268, 7 pages.
Notice of Appeal dated Oct. 10, 2008, U.S. Appl. No. 10/674,268, 2 pages.
Request for Continued Examination and Amendment and Response to Advisory Action of Sep. 30, 2008 and to Office Action of Apr. 10, 2008, dated Apr. 10, 2009, U.S. Appl. No. 10/674,268, 11 pages.
Office Action dated May 19, 2009, U.S. Appl. No. 10/674,268, 11 pages.
Office Action (Restriction Requirement) dated Jun. 17, 2005, U.S. Appl. No. 10/792,648, 10 pages.
Response to Restriction Requirement dated Jun. 29, 2005, U.S. Appl. No. 10/792,648, 8 pages.
Notice of Allowance and Fee(s) Due and Interview Summary dated Jul. 29, 2005, U.S. Appl. No. 10/792,648, 12 pages.

Request for Continued Examination dated Sep. 14, 2005, U.S. Appl. No. 10/792,648, 2 pages.
Notice of Allowance and Fee(s) Due dated Sep. 30, 2005, U.S. Appl. No. 10/792,648, 5 pages.
Request for Continued Examination dated Oct. 14, 2005, U.S. Appl. No. 10/792,648, 2 pages.
Notice of Allowance and Fee(s) Due dated Feb. 15, 2006, U.S. Appl. No. 10/792,648, 5 pages.
Restriction Requirement dated Oct. 31, 2005, U.S. Appl. NO. 10/953,328, 5 pages.
Response to Restriction Requirement dated Nov. 29, 2005, U.S. Appl. NO. 10/953,328, 8 pages.
Office Action dated Jan. 5, 2006, U.S. Appl. No. 10/953,328, 18 pages.
Amendment and Response dated Apr. 5, 2006, U.S. Appl. No. 10/953,328, 8 pages.
Office Action dated Apr. 26, 2006, U.S. Appl. No. 10/953,328, 9 pages.
Amendment and Response dated Oct. 26, 2006, U.S. Appl. No. 10/953,328, 14 pages.
Office Action (Restriction Requirement) dated Nov. 17, 2006, U.S. Appl. No. 10/953,328, 7 pages.
Response to Restriction Requirement dated Dec. 15, 2006, U.S. Appl. No. 10/953,328, 9 pages.
Final Office Action dated Jan. 18, 2007, U.S. Appl. No. 10/953,328, 13 pages.
Request for Continued Examination and Amendment and Response to Final Office Action dated Jul. 12, 2007, U.S. Appl. No. 10/953,328, 17 pages.
Final Office Action dated Aug. 7, 2007, U.S. Appl. No. 10/953,328, 11 pages.
Amendment and Response to Final Office Action dated Ocober 5, 2007, U.S. Appl. No. 10/953,328, 8 pages.
Declaration Under Rule 1.131 filed Oct. 5, 2007, U.S. Appl. No. 10/953,328, 38 pages.
Request for Continued Examination dated Oct. 29, 2007, U.S. Appl. No. 10/953,328, 2 pages.
Advisory Action dated Novmeber 1, 2007, U.S. Appl. No. 10/953,328, 4 pages.
Office Action dated Dec. 13, 2007, U.S. Appl. No. 10/953,328, 8 pages.
Declaration Under Rule 1.131 dated Feb. 12, 2008, U.S. Appl. No. 10/953,328, 2 pages.
Interview Summary dated Feb. 26, 2008, U.S. Appl. No. 10/953,328, 2 pages.
Amendment and Response to Office Action dated Apr. 14, 2008, U.S. Appl. No. 10/953,328, 28 pages.
Final Office Action dated Jun. 3, 2008, U.S. Appl. No. 10/953,328, 8 pages.
Amendment After Final (Under 37 C.F.R. 1.116) dated Nov. 3, 2008, U.S. Appl. No. 10/953,328, 19 pages.
Request for Continued Examination dated Nov. 25, 2008, U.S. Appl. No. 10/953,328, 2 pages.
Advisory Action dated Dec. 3, 2008, U.S. Appl. No. 10/953,328, 7 pages.
Final Office Action dated Jan. 21, 2009, U.S. Appl. No. 10/953,328, 9 pages.
Request for Continued Examination and Amendment and Response to Final Office Action dated May 21, 2009, U.S. Appl. No. 10/953,328, 22 pages.
Supplementary Declaration Pursuant to 37 C.F.R. 1.131 filed May 28, 2009, U.S. Appl. No. 10/953,328, 27 pages.
Interview Summary dated Jun. 1, 2009, U.S. Appl. No. 10/953,328, 3 pages.
Office Action dated Jun. 22, 2009, U.S. Appl. No. 10/953,328, 9 pages.
Office Action dated Oct. 23, 2006, U.S. Appl. No. 11/206,718, 12 pages.
Amendment and Response dated Apr. 23, 2007, U.S. Appl. No. 11/206,718, 5 pages.
Terminal Disclaimer dated Apr. 23, 2007, U.S. Appl. No. 11/206,718, 2 pages.
Notice of Allowance and Fee(s) Due dated May 16, 2007, 7 pages.
Office Action (Restriction Requirement) dated Mar. 10, 2009, U.S. Appl. No. 11/860,232, 6 pages.
Amendment and Response to Restriction Requirement dated Apr. 10, 2009, U.S. Appl. No. 11/860,232, 5 pages.
Interview Summary dated Jun. 4, 2009, U.S. Patent No. 860,232, 3 pages.

* cited by examiner

METHOD OF MAKING A SOFT GEL CAPSULE COMPRISING COQ-10 SOLUBILIZED IN A MONOTERPENE

CROSS-REFERENCE TO RELATED APPLICATION(S)

This is a Continuation application that claims benefit under 35 U.S.C. §120 to application Ser. No. 10/674,268, filed Sep. 29, 2003, entitled "Solubilized CoQ-10", the contents of which are incorporated herein in their entirety for all purposes.

FIELD OF THE INVENTION

The present invention relates to the solubilization of coenzyme Q-10 and analogs thereof in monoterpenes, thereby providing increased bioavailability in delivery.

BACKGROUND OF THE INVENTION

CoQ-10 (coenzyme Q10) is a fat-soluble quinone that is structurally similar to vitamin K and commonly known as ubiquinone. CoQ-10 is found in most living organisms, and is essential for the production of cellular energy. CoQ-10 (2,3 dimethyl-5 methyl-6-decaprenyl benzoquinone) is an endogenous antioxidant found in small amounts in meats and seafood. Although CoQ-10 is found in all human cells, the highest concentrations of CoQ-10 occur in the heart, liver, kidneys, and pancreas. It is found naturally in the organs of many mammalian species.

CoQ-10 can be synthesized in the body or it can be derived from dietary sources. Situations may arise, however, when the need for CoQ-10 surpasses the body's ability to synthesize it. CoQ-10 can be absorbed by oral supplementation as evidenced by significant increases in serum CoQ-10 levels after supplementation.

CoQ-10 is an important nutrient because it lies within the membrane of a cell organelle called the mitochondria. Mitochondria are known as the "power house" of the cell because of their ability to produce cellular energy, or ATP, by shuttling protons derived from nutrient breakdown through the process of aerobic (oxygen) metabolism. CoQ-10 also has a secondary role as an antioxidant. CoQ-10, due to the involvement in ATP synthesis, affects the function of almost all cells in the body, making it essential for the health of all human tissues and organs. CoQ-10 particularly effects the cells that are the most metabolically active: heart, immune system, gingiva, and gastric mucosa Several clinical trials have shown CoQ-10 to be effective in supporting blood pressure and cholesterol levels. Furthermore, CoQ-10 has also been shown to improve cardiovascular health. CoQ-10 has been implicated as being an essential component in thwarting various diseases such as certain types of cancers. These facts lead many to believe that CoQ-10 supplementation is vital to an individual's well being.

CoQ-10 is sparingly soluble in most hydrophilic solvents such as water. Therefore, CoQ-10 is often administered in a powdered form, as in a tablet or as a suspension. However, delivery of CoQ-10 by these methods limits the bioavailability of the material to the individual.

There is a need in the art for an improved methodology to deliver increased amount of bioavailable CoQ-10 to an individual in need thereof.

BRIEF SUMMARY OF THE INVENTION

The present invention pertains to the surprising discovery that ubiquinone (CoQ-10) can be readily dissolved in varying concentrations in monoterpenes. Generally, until the present discovery, most CoQ-10 liquid delivery methods could solubilize only up to about 5% by weight of the CoQ-10 in the "solvent". Typical solvents included various oils or the CoQ-10 was held in suspension. The present invention provides the ability to solubilize CoQ-10 in monoterpenes in concentrations of up to about 60% (weight to weight) without the need to aggressively heat the solution or with gentle warming. In particular, the solubilization of the CoQ-10 with monoterpenes can be accomplished at ambient temperatures.

In one aspect, the present invention pertains to compositions that include coenzyme Q-10 or an analog thereof with a sufficient quantity of a monoterpene that is suitable to solubilize said coenzyme Q-10 and a pharmaceutically acceptable carrier. Generally, about 30 to about 45% of the CoQ-10 (by weight) is solubilized in the monoterpene. In particular, the monoterpene is limonene. The compositions of the invention are useful as dietary supplements or as nutriceuticals.

In particular, the compositions of the invention are included in a soft gelatin (soft gel) capsule. Typically, the soft gelatin capsule includes at least 5% by weight of coenzyme Q-10 or an analog thereof solubilized in a monoterpene. Typical monoterpenes include, for example, perillyl alcohol, perillic acid, cis-dihydroperillic acid, trans-dihydroperillic acid, methyl esters of perillic acid, methyl esters of dihydroperillic acid, limonene-2-diol, uroterpenol, and combinations thereof.

In another embodiment, the present invention pertains to methods for delivery of an effective amount of bioavailable CoQ-10 to an individual. The method includes providing CoQ-10 solubilized in a monoterpene, such that an effective amount of CoQ-10 is provided to the individual.

In still another embodiment, the present invention also includes packaged formulations of the invention that include a monoterpene as a solvent for the CoQ-10 and instructions for use of the tablet, capsule, elixir, etc.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The present invention pertains to the surprising discovery that ubiquinone (CoQ-10) can be readily dissolved in varying concentrations in monoterpenes. CoQ-10 is found in most living organisms, and is essential for the production of cellular energy. Ubiquinone is a naturally occurring hydrogen carrier in the respiratory chain (coenzyme Q) and structurally, it is a 2,3-dimethoxy-5-methyl-1,4-benzoquinone with a multiprenyl side chain, the number of isoprene units varying depending upon the organism from which it is derived. CoQ-10 analogs include reduced and semi-reduced CoQ-10 and ubiquinone derivatives described, for example, in WO 8803015, the teachings of which are incorporated herein by reference.

Generally, until the present discovery, most CoQ-10 liquid delivery methods could solubilize only up at most about 10% by weight of the CoQ-10 in the "solvent. Typical solvents included oils or the CoQ-10 was held in an aqueous suspension. Alternatively, the CoQ-10 was provided as a solid in a tablet or powder.

The present invention provides the ability to solubilize CoQ-10 in monoterpenes, as defined herein, in concentrations of up to about 60% (weight to weight) without the need to heat the solution. In one aspect, the monoterpene solubilizes CoQ-10 from about 0.1 percent by weight to about 45 percent by weight.

In particular, the solubilization of the CoQ-10 with monoterpenes can be accomplished at ambient temperatures. In one aspect, from about 5 to about 50 percent (weight CoQ-10/weight solvent) CoQ-10 can be solubilized in a monoterpene. In another aspect, from about 15 to about 40 percent w/w can be solubilized and in still another aspect, from about 20 to about 35 percent w/w CoQ-10 can be solubilized in a monoterpene.

The phrase "sufficient quantity of a monoterpene suitable to solubilize coenzyme Q-10" is therefore intended to mean that that amount of a monoterpene that will dissolve CoQ-10 under a given set of conditions, generally, those at ambient temperature. This determination should be understood by one skilled in the art and can be determined by methods known in the art, such as by solubility studies.

One of the particular advantages of utilizing monoterpenes in combination with CoQ-10 is that the enzyme is dissolved by the monoterpene. That is, many formulations currently in the marketplace have CoQ-10 present as a suspension; a situation where not all the CoQ-10 is dissolved. This reduces efficacy and the bioavailability of the CoQ-10. The present invention eliminates this disadvantage by solubilizing the CoQ-10 in the monoterpene.

A particular advantage in using monoterpenes is that the CoQ-10 does not have to be heated to dissolve into solution. This is important so that the CoQ-10 does not degrade upon dissolution.

The term "monoterpene" as used herein, refers to a compound having a 10-carbon skeleton with non-linear branches. A monoterpene refers to a compound with two isoprene units connected in a head-to-end manner. The term "monoterpene" is also intended to include "monoterpenoid", which refers to a monoterpene-like substance and may be used loosely herein to refer collectively to monoterpenoid derivatives as well as monoterpenoid analogs. Monoterpenoids can therefore include monoterpenes, alcohols, ketones, aldehydes, ethers, acids, hydrocarbons without an oxygen functional group, and so forth.

It is common practice to refer to certain phenolic compounds, such as eugenol, thymol and carvacrol, as monoterpenoids because their function is essentially the same as a monoterpenoid. However, these compounds are not technically "monoterpenoids" (or "monoterpenes") because they are not synthesized by the same isoprene biosynthesis pathway, but rather by production of phenols from tyrosine. However, common practice will be followed herein. Suitable examples of monoterpenes include, but are not limited to, limonene, pinene, cintronellol, terpinene, nerol, menthane, carveol, S-linalool, safrol, cinnamic acid, apiol, geraniol, thymol, citral, carvone, camphor, etc. and derivatives thereof. For information about the structure and synthesis of terpenes, including terpenes of the invention, see Kirk-Othmer Encyclopedia of Chemical Technology, Mark, et al., eds., 22:709-762 3d Ed (1983), the teachings of which are incorporated herein in their entirety.

In particular, suitable limonene derivatives include perillyl alcohol, perillic acid, cis-dihydroperillic acid, trans-dihydroperillic acid, methyl esters of perillic acid, methyl esters of dihydroperillic acid, limonene-2-diol, uroterpenol, and combinations thereof.

Formulation of the CoQ-10 can be accomplished by many methods known in the art. For example, the solubilized CoQ-10 can be formulated in a suspension, an emulsion, an elixir, a solution, a caplet that harbors the liquid, or in a soft gelatin capsule. Often the formulation will include an acceptable carrier, such as an oil, or other suspending agent.

Suitable carriers include but are not limited to, for example, fatty acids, esters and salts thereof, that can be derived from any source, including, without limitation, natural or synthetic oils, fats, waxes or combinations thereof. Moreover, the fatty acids can be derived, without limitation, from non-hydrogenated oils, partially hydrogenated oils, fully hydrogenated oils or combinations thereof. Non-limiting exemplary sources of fatty acids (their esters and salts) include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, flaxseed oil, evening primrose oil, jojoba, tallow, beef tallow, butter, chicken fat, lard, dairy butterfat, shea butter or combinations thereof.

Specific non-limiting exemplary fish or marine oil sources include shellfish oil, tuna oil, mackerel oil, salmon oil, menhaden, anchovy, herring, trout, sardines or combinations thereof. In particular, the source of the fatty acids is fish or marine oil (DHA or EPA), soybean oil or flaxseed oil. Alternatively or in combination with one of the above identified carrier, beeswax can be used as a suitable carrier, as well as suspending agents such as silica (silicon dioxide).

The formulations of the invention are considered dietary supplements useful to the increase the amounts of CoQ-10 in the individuals in need thereof.

Alternatively, the formulations of the invention are also considered to be nutraceuticals. The term "nutraceutical" is recognized in the art and is intended to describe specific chemical compounds found in foods that may prevent disease. CoQ-10 is one such compound.

The formulations of the invention can further include various ingredients to help stabilize, or help promote the bioavailability of the CoQ-10, or serve as additional nutrients to an individual's diet. Suitable additives can include vitamins and biologically-acceptable minerals. Non-limiting examples of vitamins include vitamin A, B vitamins, vitamin C, vitamin D, vitamin E, vitamin K and folic acid. Non-limiting examples of minerals include iron, calcium, magnesium, potassium, copper, chromium, zinc, molybdenum, iodine, boron, selenium, manganese, derivatives thereof or combinations thereof. These vitamins and minerals may be from any source or combination of sources, without limitation. Non-limiting exemplary B vitamins include, without limitation, thiamine, niacinamide, pyridoxine, riboflavin, cyanocobalamin, biotin, pantothenic acid or combinations thereof.

Vitamin(s), if present, are present in the composition of the invention in an amount ranging from about 5 mg to about 500 mg. More particularly, the vitamin(s) is present in an amount ranging from about 10 mg to about 400 mg. Even more specifically, the vitamin(s) is present from about 250 mg to about 400 mg. Most specifically, the vitamin(s) is present in an amount ranging from about 10 mg to about 50 mg. For example, B vitamins are in usually incorporated in the range of about 1 milligram to about 10 milligrams, i.e., from about 3 micrograms to about 50 micrograms of B12. Folic acid, for example, is generally incorporated in a range of about 50 to about 400 micrograms, biotin is generally incorporated in a range of about 25 to about 700 micrograms and cyanocobalamin is incorporated in a range of about 3 micrograms to about 50 micrograms.

Mineral(s), if present, are present in the composition of the invention in an amount ranging from about 25 mg to about 1000 mg. More particularly, the mineral(s) are present in the composition ranging from about 25 mg to about 500 mg. Even more particularly, the mineral(s) are present in the composition in an amount ranging from about 100 mg to about 600 mg.

Various additives can be incorporated into the present compositions. Optional additives of the present composition include, without limitation, phospholipids, L-carnitine, starches, sugars, fats, antioxidants, amino acids, proteins, flavorings, coloring agents, hydrolyzed starch(es) and derivatives thereof or combinations thereof.

As used herein, the term "phospholipid" is recognized in the art, and refers to phosphatidyl glycerol, phosphatidyl inositol, phosphatidyl serine, phosphatidyl choline, phosphatidyl ethanolamine, as well as phosphatidic acids, ceramides, cerebrosides, sphingomyelins and cardiolipins.

L-carnitine is recognized in the art and facilitates transport of materials through the mitochondrial membrane. L-carnitine is an essential fatty acid metabolism cofactor that helps to move fatty acids to the mitochondria from the cytoplasm. This is an important factor as this is where CoQ-10 uptake occurs.

In one aspect of the present invention, L-carnitine is included in soft gel formulations in combination with CoQ-10. Suitable ratios of L-carnitine and CoQ-10 are known in the art and include those described in U.S. Pat. No. 4,599,232, issued to Sigma Tau Industrie Faramaceutiche Riunite S.p.A. on Jul. 8, 1986, the teachings of which are incorporated herein in their entirety. In particular, combinations of limonene, CoQ-10 and L-carnitine in soft gel formulations are of importance. The present invention provides the advantage of solvating large amounts (relative to that of current state of the art) of CoQ-10 in limonene in a soft gel capsule along with an additive, such as L-carnitine.

As used herein, the term "antioxidant" is recognized in the art and refers to synthetic or natural substances that prevent or delay the oxidative deterioration of a compound. Exemplary antioxidants include tocopherols, flavonoids, catechins, superoxide dismutase, lecithin, gamma oryzanol; vitamins, such as vitamins A, C (ascorbic acid) and E and beta-carotene; natural components such as camosol, carnosic acid and rosmanol found in rosemary and hawthorn extract, proanthocyanidins such as those found in grapeseed or pine bark extract, and green tea extract.

The term "flavonoid" as used herein is recognized in the art and is intended to include those plant pigments found in many foods that are thought to help protect the body from cancer. These include, for example, epi-gallo catechin gallate (EGCG), epi-gallo catechin (EGC) and epi-catechin (EC).

Any dosage form, and combinations thereof, are contemplated by the present invention. Examples of such dosage forms include, without limitation, chewable tablets, elixirs, liquids, solutions, suspensions, emulsions, capsules, soft gelatin capsules, hard gelatin capsules, caplets, lozenges, chewable lozenges, suppositories, creams, topicals, ingestibles, injectables, infusions, health bars, confections, animal feeds, cereals, cereal coatings, and combinations thereof. The preparation of the above dosage forms are well known to persons of ordinary skill in the art.

For example, health bars can be prepared, without limitation, by mixing the formulation plus excipients (e.g., binders, fillers, flavors, colors, etc.) to a plastic mass consistency. The mass is then either extended or molded to form "candy bar" shapes that are then dried or allowed to solidify to form the final product.

Soft gel or soft gelatin capsules can be prepared, for example, without limitation, by dispersing the formulation in an appropriate vehicle (e.g. rice bran oil, monoterpene and/or beeswax) to form a high viscosity mixture. This mixture is then encapsulated with a gelatin based film using technology and machinery known to those in the soft gel industry. The industrial units so formed are then dried to constant weight. Typically, the weight of the capsule is between about 100 to about 2500 milligrams and in particular weigh between about 1500 and about 1900 milligrams, and more specifically can weigh between about 1500 and about 2000 milligrams.

For example, when preparing soft gelatin shells, the shell can include between about 20 to 70 percent gelatin, generally a plasticizer and about 5 to about 60% by weight sorbitol. The filling of the soft gelatin capsule is liquid (principally limonene, in combination with rice bran oil and/or beeswax if desired) and can include, apart form the antioxidant actives, a hydrophilic matrix. The hydrophilic matrix, if present, is a polyethylene glycol having an average molecular weight of from about 200 to 1000. Further ingredients are optionally thickening agents. In one embodiment, the hydrophilic matrix includes polyethylene glycol having an average molecular weight of from about 200 to 1000, 5 to 15% glycerol, and 5 to 15% by weight of water. The polyethylene glycol can also be mixed with propylene glycol and/or propylene carbonate.

In another embodiment, the soft gel capsule is prepared from gelatin, glycerine, water and various additives. Typically, the percentage (by weight) of the gelatin is between about 30 and about 50 weight percent, in particular between about 35 and about weight percent and more specifically about 42 weight percent. The formulation includes between about 15 and about 25 weight percent glycerine, more particularly between about 17 and about 23 weight percent and more specifically about 20 weight percent glycerine.

The remaining portion of the capsule is typically water. The amount varies from between about 25 weigh percent and about 40 weight percent, more particularly between about 30 and about 35 weight percent, and more specifically about 35 weight percent. The remainder of the capsule can vary, generally, between about 2 and about 10 weight percent composed of a flavoring agent(s), sugar, coloring agent(s), etc. or combination thereof. After the capsule is processed, the water content of the final capsule is often between about 5 and about 10 weight percent, more particularly 7 and about 12 weight percent, and more specifically between about 9 and about 10 weight percent.

As for the manufacturing, it is contemplated that standard soft shell gelatin capsule manufacturing techniques can be used to prepare the soft-shell product. Examples of useful manufacturing techniques are the plate process, the rotary die process pioneered by R. P. Scherer, the process using the Norton capsule machine, and the Accogel machine and process developed by Lederle. Each of these processes are mature technologies and are all widely available to any one wishing to prepare soft gelatin capsules.

Typically, when a soft gel capsule is prepared, the total weight is between about 250 milligrams and about 2.5 gram in weight, e.g., 400-750 milligrams. Therefore, the total weight of additives, such as vitamins and antioxidants, is between about 80 milligrams and about 2000 milligrams, alternatively, between about 100 milligrams and about 1500 milligrams, and in particular between about 120 milligrams and about 1200 milligrams.

For example, a soft gel capsule can be prepared by mixing a 35% solution of CoQ-10 and limonene (w/w) (e.g., 104 milligrams of CoQ-10 in 193.14 milligrams of limonene) with between about 0.01 grams and about 0.4 grams (e.g., 0.1 grams) tocopherol, between about 200 grams and about 250 grams (e.g., 225 grams) rice bran oil and between about 0.01 grams and about 0.5 grams betacarotene (e.g. about 0.02 grams). The mixture is then combined with encapsulated within a gelatin capsule as described above.

The present invention also provides packaged formulations of a monoterpene with CoQ-10 and instructions for use of the tablet, capsule, elixir, etc. Typically, the packaged formulation, in whatever form, is administered to an individual in need thereof that requires and increase in the amount of CoQ-10 in the individual's diet. Typically, the dosage requirements is between about 1 to about 4 dosages a day.

CoQ-10 has been implicated in various biochemical pathways and is suitable for the treatment of cardiovascular conditions, such as those associated with, for example, statin drugs that effect the body's ability to product coQ-10 naturally. CoQ-10 has also been implicated in various periodontal diseases. Furthermore, CoQ-10 has been implicated in mitochondrial related diseases and disorders, such as the inability to product acetyl coenzyme A, neurological disorders, for example, such as Parkinson's disease and, Prater-Willey syndrome.

The following examples are intended to be illustrative only and should not be considered limiting.

EXAMPLES

Formulations of CoQ-10 can be prepared in the following ratios by mixing the components together and then placing into a soft gel capsule.

| Component | Example 1 | Example 2 |
| --- | --- | --- |
| CoQ-10 | 104.09 mg | 104.09 mg |
| Mixed Tocopherols (372 IU/g) | 269.03 mg | 269.03 mg |
| Rice Bran Oil | 176.02 mg | — |
| Natural Beta Carotene (20% by weight) | 10.05 mg | 10.05 mg |
| Yellow Beeswax | 20.0 mg | — |
| D-limonene | — | 196.02 mg |
| Total weight | 580 mg | 580 mg |

Example 2 demonstrates that the use of limonene solubilizes CoQ-10 without the requirement of beeswax and/or rice bran oil being present. Examples 1 and 2 could be incorporated into soft gel capsules by standard methods known in the art.

| Component | Example 3 | Example 4 |
| --- | --- | --- |
| CoQ-10 | 17.95 g | 17.95 g |
| EPAX 2050TG | 48.77 g | 45.49 g |
| D-Limonene | 35.70 g | 35.70 g |
| 5-67 Tocopherol (1000 IU/g) | — | 0.86 g |

Examples 3 and 4 demonstrate that CoQ-10 can be solubilized in scalable quantities. Additives, such as EPAX 2050TG (an ω-3 oil; 20% EPA/50% DHA as triglycerides, remainder fatty acid/triglycerides; Pronova Biocare) and tocopherols (5-67 Tocopherol; BD Industries) can easily be incorporated into such limonene containing formulations. The resultant mixtures contained approximately 100 mg of CoQ-10 per soft gel capsule. Preparation of the soft gel capsules was accomplished by methods well known in the art.

Although the present invention has been described with reference to preferred embodiments, persons skilled in the art will recognize that changes may be made in form and detail without departing from the spirit and scope of the invention.

All literature and patent references cited throughout the application are incorporated by reference into the application for all purposes.

What is claimed is:

1. A method of preparing a soft gel capsule, comprising the steps of:
   (a) mixing coenzyme Q-10 with a sufficient quantity of a monoterpene suitable to dissolve said coenzyme Q-10 and form a solution, with the proviso that said solution is not part of an emulsion, suspension, or elixir; wherein the amount of coenzyme Q-10 in said solution is about 15% up to about 60% coenzyme Q-10 by weight;
   (b) mixing said solution with an acceptable carrier to form a composition, with the proviso that said composition is not an emulsion, suspension, or elixir; and
   (c) encapsulating said composition in a soft gel capsule.

2. The method of claim 1, wherein said coenzyme Q-10 is selected from the group consisting of coenzyme Q-10, reduced coenzyme Q-10 and semi-reduced coenzyme Q-10.

3. The method of claim 1, wherein said monoterpene is limonene or a derivative thereof.

4. The method of claim 3, wherein said limonene derivative is selected from the group consisting of perillyl alcohol, perillic acid, cis-dihydroperillic acid, trans-dihydroperillic acid, a methyl ester of perillic acid, a methyl ester of dihydroperillic acid, limonene-2-diol, uroterpenol, and a combination thereof.

5. The method of claim 1, further comprising the step of adding rice bran oil or beeswax to the composition.

6. The method of claim 1, wherein said coenzyme Q-10 is solubilized in said monoterpene in an amount of about 15% to about 40% by weight at room temperature.

7. The method of claim 1, further comprising the step of adding vitamin E to the composition.

8. The method of claim 1, further comprising the step of adding a seed oil to the composition.

9. The method of claim 1, further comprising the step of adding a fish oil to the composition.

10. The method of claim 1, further comprising the step of adding an antioxidant to the composition.

11. The method of claim 1, wherein said mixing coenzyme Q-10 with a sufficient quantity of a monoterpene is at room temperature.

12. The method of claim 1, wherein said coenzyme Q-10 is solubilized in said monoterpene in an amount of about 20% to about 40% by weight at room temperature.

13. The method of claim 1, wherein said coenzyme Q-10 is solubilized in said monoterpene in an amount of about 15% to about 50% by weight at room temperature.

14. The method of claim 1, wherein said coenzyme Q-10 is solubilized in said monoterpene in an amount of about 20% to about 60% by weight at room temperature.

15. The method of claim 1, wherein said coenzyme Q-10 is solubilized in said monoterpene in an amount of about 40% to about 60% by weight at room temperature.

* * * * *